(12) United States Patent
Faulkner et al.

(10) Patent No.: US 9,655,516 B2
(45) Date of Patent: May 23, 2017

(54) COMPACT MOBILE DILATION TABLE

(71) Applicants: Martin Lee Faulkner, Marion, AR (US); Johnny D. Faulkner, Marion, AR (US)

(72) Inventors: Martin Lee Faulkner, Marion, AR (US); Johnny D. Faulkner, Marion, AR (US)

(*) Notice: Subject to any disclaimer, the term of this patent is extended or adjusted under 35 U.S.C. 154(b) by 268 days.

(21) Appl. No.: 14/631,291

(22) Filed: Feb. 25, 2015

(65) Prior Publication Data

US 2015/0238080 A1    Aug. 27, 2015

Related U.S. Application Data

(60) Provisional application No. 61/944,066, filed on Feb. 25, 2014.

(51) Int. Cl.
*A61B 3/00* (2006.01)
*A61B 3/12* (2006.01)
*G03B 15/14* (2006.01)

(52) U.S. Cl.
CPC ............... *A61B 3/12* (2013.01); *A61B 3/00* (2013.01); *A61B 3/0083* (2013.01); *G03B 15/14* (2013.01)

(58) Field of Classification Search
CPC ..... A61B 3/00; A61B 3/12; A61B 3/18; A61B 3/185
USPC ........................... 351/200, 206, 145
See application file for complete search history.

(56) References Cited

U.S. PATENT DOCUMENTS

| | | | |
|---|---|---|---|
| 5,220,360 A | * | 6/1993 | Verdooner ............... A61B 3/12 351/212 |
| 2008/0035159 A1 | * | 2/2008 | Perez-Cruet ........... A61B 6/107 128/849 |
| 2009/0136101 A1 | * | 5/2009 | Chhibber ............... A61B 5/442 382/128 |

* cited by examiner

*Primary Examiner* — Huy K Mai
(74) *Attorney, Agent, or Firm* — Butler Snow LLP

(57) ABSTRACT

A dilation tower providing a darkened space for performing a dilated fundus examination (DFE) in bright environments (e.g., stores, shopping malls, shopping centers, medical offices, etc.) is provided. In order to reach more patients in need of DFEs, the dilation tower provided may be configured to be mobile. A method of administering a DFE on a patient comprising the steps of positioning said patient in a patient area of a dilation tower, enclosing said patient and said patient area with a patient area cloak, and performing said DFE on said patient is also provided.

19 Claims, 13 Drawing Sheets

COMPACT MOBILE DILATION TABLE

CROSS-REFERENCES TO RELATED APPLICATIONS

This application claims priority to U.S. provisional patent application Ser. No. 61/944,066 to Martin Lee Faulkner and Johnny D. Faulkner filed Feb. 25, 2014, which is hereby incorporated by reference in its entirety.

FIELD OF THE INVENTION

The present invention is generally directed toward a new dilation tower providing a darkened space for performing a dilated fundus examination.

BACKGROUND OF THE INVENTION

Vision loss due to illnesses of the eye, whether caused by acute disease of the eye (e.g., glaucoma) or systemic disease (e.g., diabetes), currently has a major impact on the economy and the overall public health. Many conditions that lead to vision loss are considered treatable, and early detection and intervention may have a profound effect on course of disease and prognosis. There is some evidence that many in the population are not receiving regular or even recommended eye examinations. The most common eye exam for detecting issues with eye health is the dilated fundus examination ("DFE"). DFEs often require chemical dilation of the eye (i.e., mydriasis); however, some non-mydriatic retinal camera systems are currently in use. Current techniques and equipment require DFEs to be given in a dark room, such as a medical office, and are commonly provided by opticians and other medical professionals in the field. As such, DFEs are not amenable to mass marketing in high traffic areas, such as shopping and/or commercial centers.

SUMMARY OF THE INVENTION

According to one aspect of the present invention, a dilation tower is provided with a right tower, a left tower, a tower table base unit, a tower table, a patient side, wherein the patient side comprises a patient area defined by a patient area cloak, and a medical professional side. The present invention solves the problems in the prior art by providing a compact apparatus with a dark environment for conducting a DFE for a patient in an otherwise bright environment.

According to another advantageous feature of the present invention, the dilation tower may be configured for mobility. According to yet another advantageous feature of the present invention, the dilation tower may be configured to have automatic DFE equipment. According to yet another advantageous feature of the present invention, the dilation tower may be configured to have a patient area cloak that extends to the surface of the tower table. According to yet another advantageous feature of the present invention, the dilation tower may be configured to have a patient area cloak that extends beyond the surface of the tower table. According to yet another advantageous feature of the present invention, the dilation tower may be configured to have a patient area cloak that extends to the floor. According to yet another advantageous feature of the present invention, the dilation tower may be configured to have a patient area cloak incorporating one or more flaps to further limit environmental light from entering said patient area. According to yet another advantageous feature of the present invention, the dilation tower may be configured to have patient area cloak arms for supporting said patient area cloak. According to yet another advantageous feature of the present invention, the dilation tower may be configured to have patient area cloak arms that are extendable and retractable. According to yet another advantageous feature of the present invention, the dilation tower may be configured to have patient area cloak arms that are independently extendable and retractable. According to yet another advantageous feature of the present invention, the dilation tower may be configured to have patient area cloak arms that move about a tower bridge to expand or contract the patient area. According to yet another advantageous feature of the present invention, the dilation tower may be configured to have patient area cloak arms that swivel or pivot to expand or retract the patient area. According to yet another advantageous feature of the present invention, the dilation tower may be configured to have multimedia players. According to yet another advantageous feature of the present invention, the dilation tower may be configured to have a patient seat in the patient area. According to yet another advantageous feature of the present invention, the dilation tower may be configured to receive and distribute electrical power. According to yet another advantageous feature of the present invention, the dilation tower may be configured to have a tower table that is height adjustable.

According to another aspect of the present invention, a method of administering a DFE to a patient in a bright environment comprising the steps of positioning said patient in a patient area of a dilation tower, enclosing said patient and said patient area with a patient area cloak, and performing said DFE on said patient. The present invention solves the problems in the prior art by providing a method for administering a DFE to a patient in a bright environment.

BRIEF DESCRIPTION OF THE DRAWINGS

Further advantages of the invention will become apparent by reference to the detailed description of preferred embodiments when considered in conjunction with the drawings.

DETAILED DESCRIPTION

The following detailed description is presented to enable any person skilled in the art to make and use the invention. For purposes of explanation, specific details are set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

Figure 1:
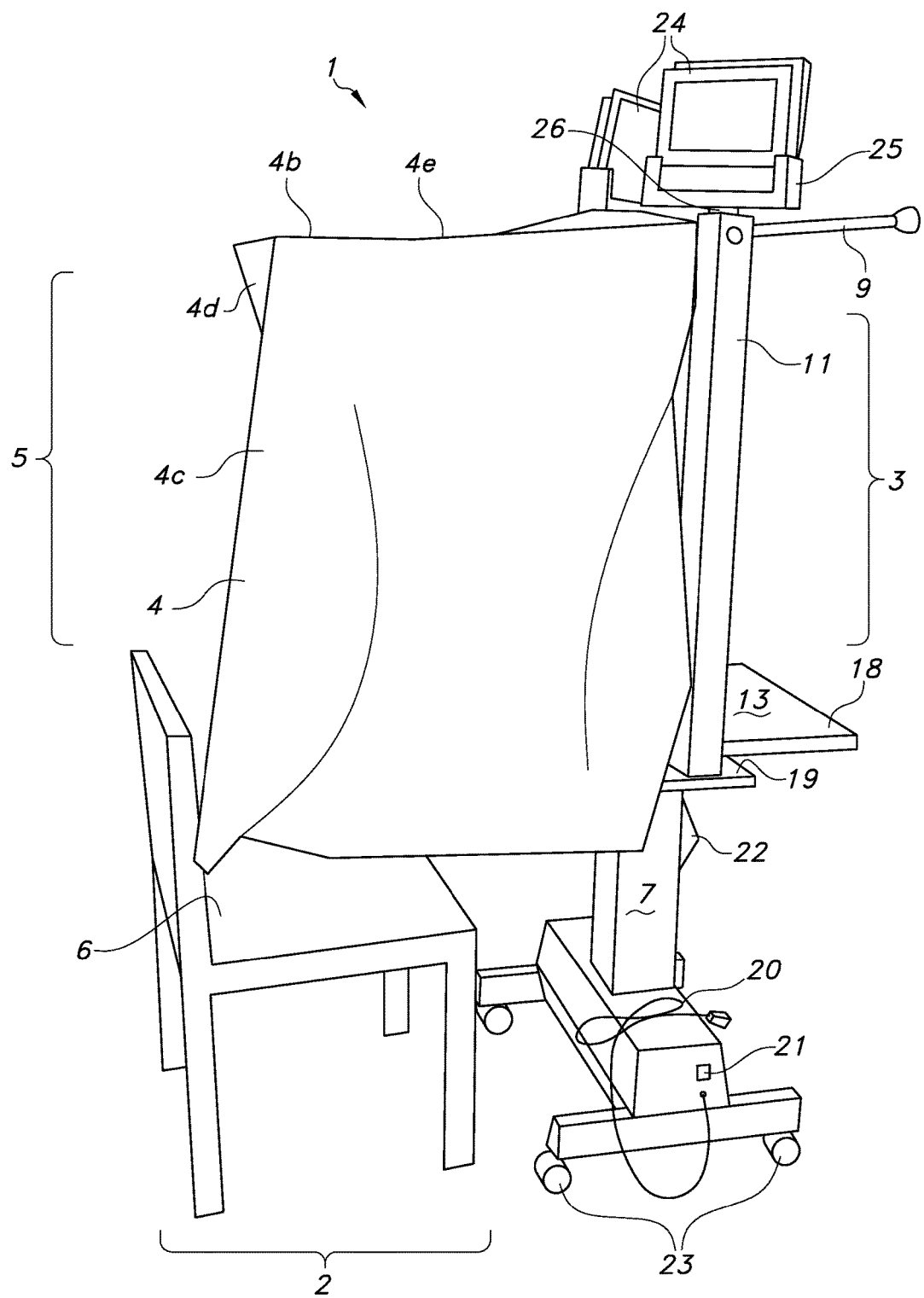
FIG. 1 is an exemplary embodiment of the disclosed dilation tower with patient area cloak.
Figure 7:
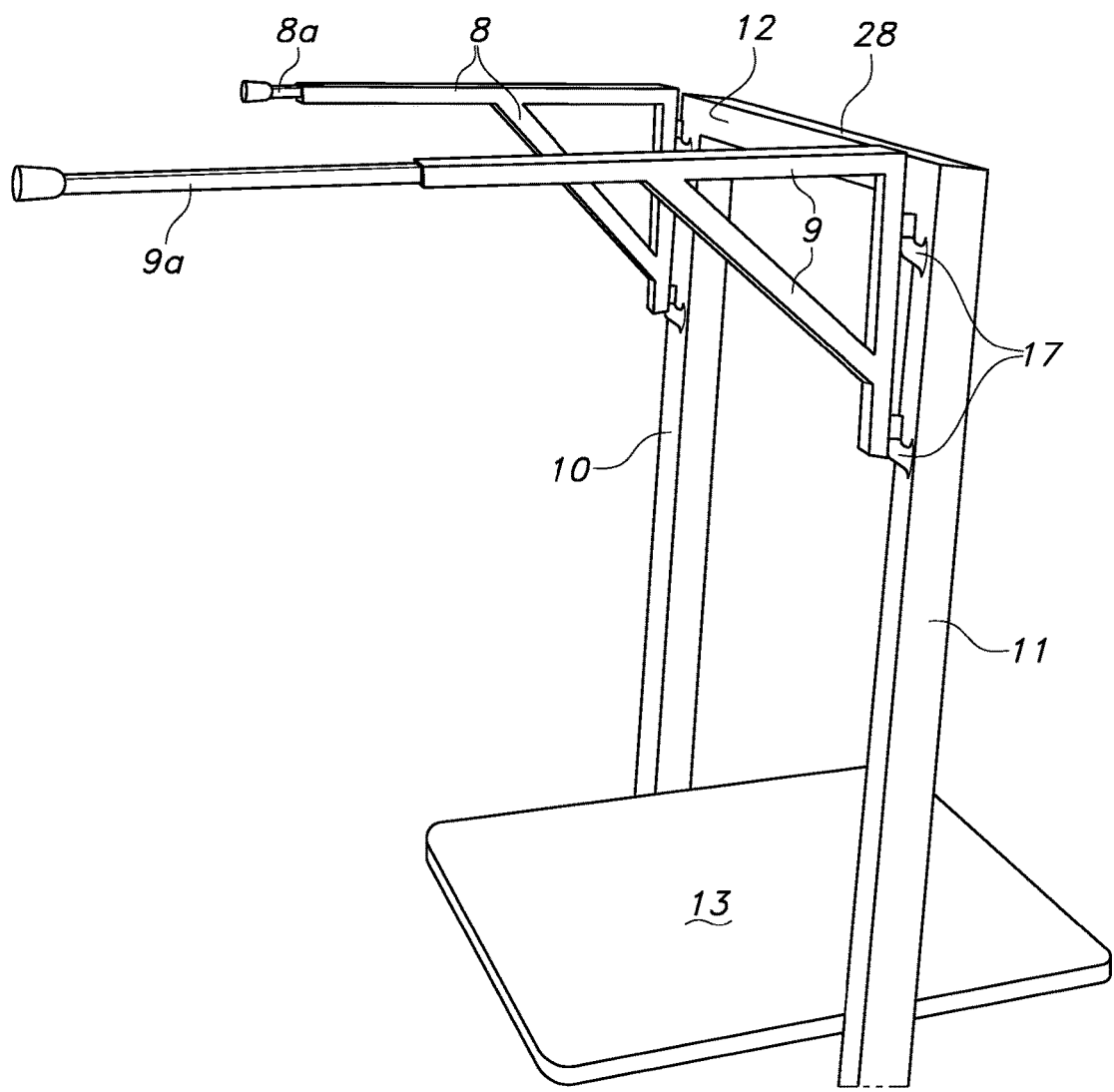
FIG. 7 is another exemplary embodiment of the disclosed dilation tower having independently extendable patient area cloak arms with swivel mounting members.
Figure 11:
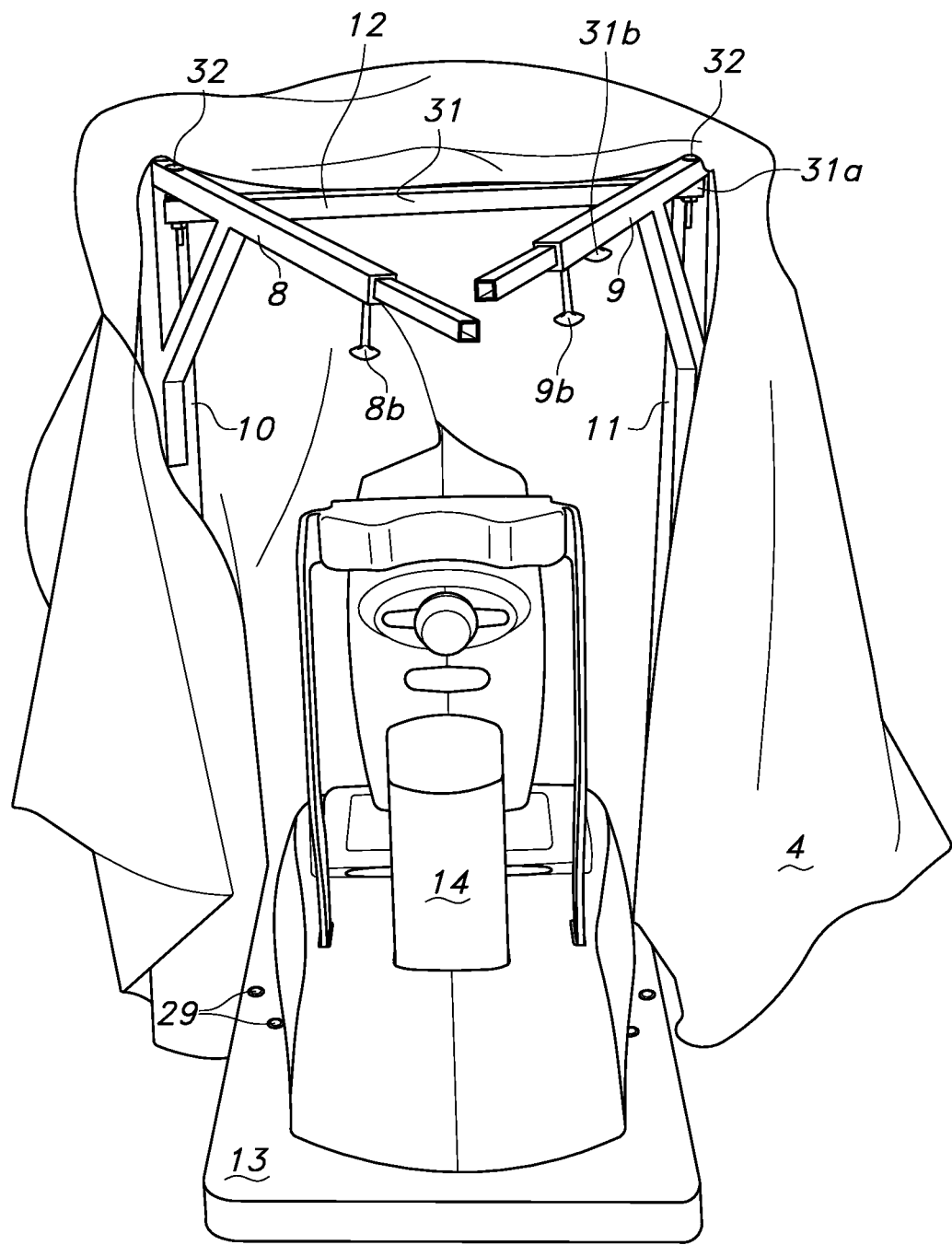
FIG. 11 shows the dilation tower of FIG. 10 from the patient area side with cloak pulled back from adjustable cloak arms in a non-extended and swiveled narrow position but maintaining cloak first side partitioning medical professional side from the patient area side.

Referring to the drawings, FIG. 1 illustrates an exemplary embodiment of the disclosed invention. The dilation tower 1 depicted in FIG. 1 has a patient side 2 and a medical professional side 3. The patient side 2 is provided with a patient area cloak 4 over and defining a patient area 5 that includes a place for a patient to sit (e.g., patient seat 6) during the examination. Although an unattached chair 6 is shown in FIG. 1 as the place for a patient to sit, it is contemplated that a dilation tower 1 of the present invention could be equipped with a patient seat 6 that is physically attached to or made part of the tower table base unit 7. In some embodiments, the patient area cloak 4 is disposed on a right and a left patient area cloak arm 8,9. Preferably, the right and left patient area cloak arms 8,9 are extendable in the direction of the patient side 2 to a desired length in order to completely cover the occupied patient area. Therefore, the right and left patient area cloak arms 8,9 are preferably retractable in the direction of the medical professional side 3. The retraction/extension of the right and left patient area cloak arms 8,9 can be accomplished by any known means, for example telescoping arms, sliding arms, and tension arms. More preferably, right and left patient area cloak arms 8,9 are independently extendable/retractable with right and left arm extension members 8a and 9a (see FIG. 7). As shown in FIG. 11, right and left patient area cloak arms 8,9 also preferably include set screws 8b,9b to maintain the desired length.

Figure 5:
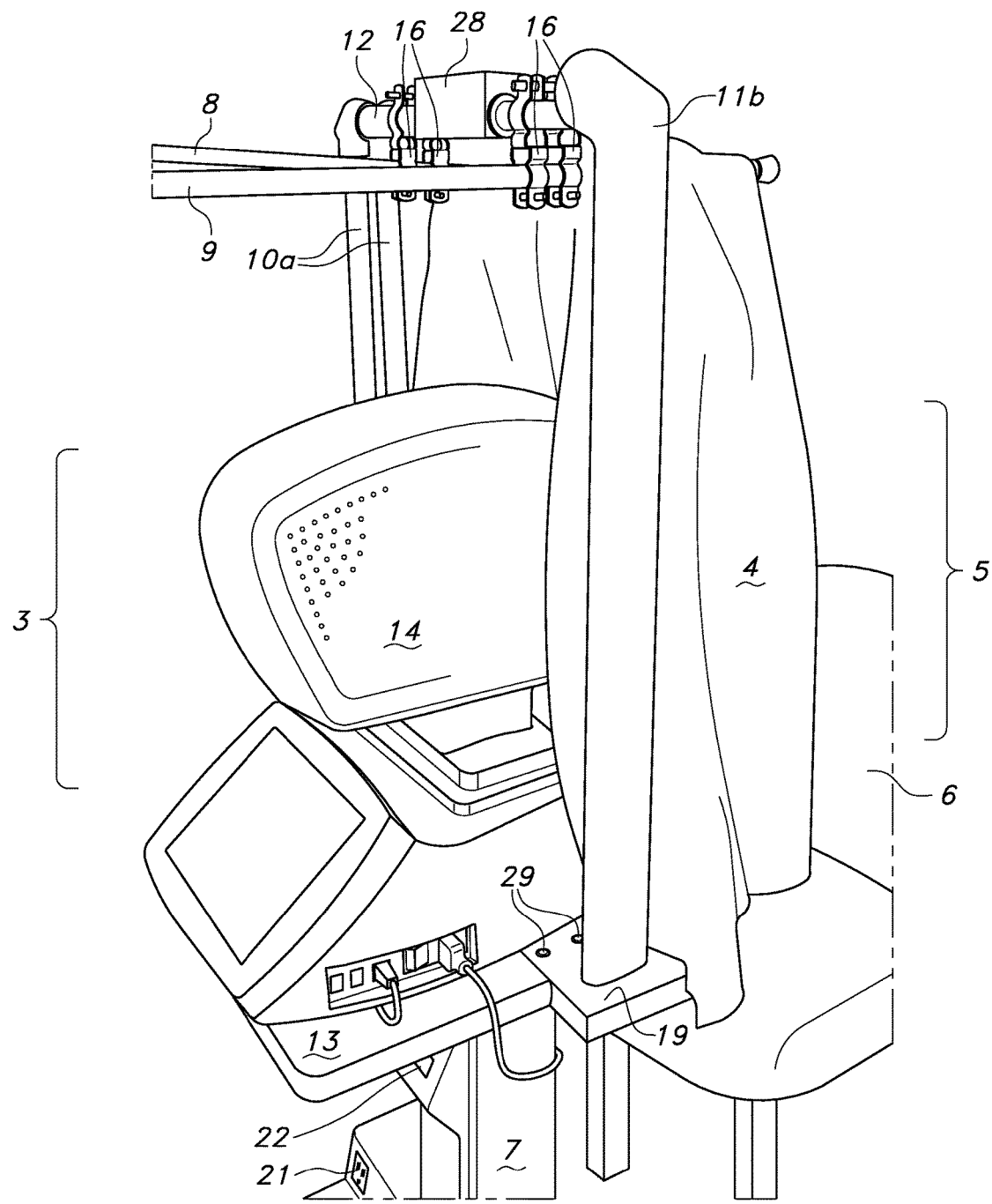
FIG. 5 is another exemplary embodiment of the disclosed dilation tower with patient area cloak and digital retina scanning equipment.

The dilation tower 1 of the present invention is designed to be mobile and for placement in high traffic areas, such as shopping malls, stores, etc., where patients can be solicited to undertake a DFE. While such high traffic areas provide access to target patients who need or may need a DFE, these environments present too much light for a DFE to be performed properly. The patient area cloak 4 functions to create a dark environment for the patient and the patient area 5 of the DFE equipment 14. As shown in FIG. 5, DFE equipment 14 will normally be positioned to span patient side 2 and medical professional side 3. The patient area cloak 4 can be made from any suitable material (or fabric) to block ambient light from the surrounding environment. Preferably, the material of patient area cloak 4 will be opaque or substantially opaque. The patient area cloak 4 can be constructed to comprise more than one layer of material or fabric in order to be opaque or substantially opaque.

The patient area cloak 4 is designed to have a first side 4a, which extends between a right and a left tower 10,11 and down from the tower bridge 12 to a tower table equipment surface 13 in order to the to create a light barrier or "wall" between the patient area 5 and the medical professional side 3. The first side 4a should provide sufficient material to encounter DFE equipment 14 and still reach the tower table equipment surface 13. In some embodiments, first side 4a may extend down beyond the tower table equipment surface 13 to further block light. In some such embodiments, first side 4a may extend down to the floor or substantially to the floor. First side 4a may be affixed to the right and the left tower 10,11, the tower bridge 12, and the tower table equipment surface 13 by any suitable fastener, such as hook and loop fasteners, magnets, or an adhesive. In preferred embodiments, the first side 4a is kept taught or relatively taught to the DFE equipment 14 by means of elastic, cinch or drawstring, hook and loop fasteners, adhesive, or other suitable means. Such may be accomplished by including an opening(s) or hole(s) in the first side 4a for positioning part of the DFE equipment 14 through. Preferably, first side 4a may be temporarily affixed to the dilation tower 1 to permit removal for maintenance, cleaning, etc. of first side 4a.

The patient area cloak 4 is designed to have a second (right) side 4b, which extends down from the right patient area cloak arm 8. The second (right) side 4b should extend down sufficiently to provide a dark environment for the patient and the DFE equipment 14. In some embodiments, second (right) side 4b will extend at least to the tower table equipment surface 13. In other embodiments, second (right) side 4b may extend down beyond the tower table equipment surface 13 to further block light. In some such embodiments, second (right) side 4b may extend down to the floor or substantially to the floor. Second (right) side 4b may be affixed to the right tower 10 by any suitable fastener, such as hook and loop fasteners, magnets, or an adhesive. Preferably, second (right) side 4b may be temporarily affixed to the dilation tower 1 to permit removal for maintenance, cleaning, etc. of second (right) side 4b. In preferred embodiments where the right patient area cloak arm 8 is extendable/retractable, second (right) side 4b is designed to accommodate the full extension/retraction thereof. Second (right) side 4b may be affixed to right patient area cloak arm 8 by any convenient means to accomplish the goals of blocking light and, where applicable, extension/retraction of the material. For example, the second (right) side 4b may be affixed by hook and loop fastener, adhesive, curtain rings/hooks or similar device, by inserting right patient area cloak arm 8 through second (right) side 4b, etc. Second (right) side 4b may be designed to be stationary (i.e., only extendable/retractable when right patient area cloak arm 8 is extended/retracted) or independently extendable/retractable along right patient area cloak arm 8.

The patient area cloak 4 is designed to have a third (left) side 4c, which extends down from the left patient area cloak arm 9. The third (left) side 4c should extend down sufficiently to provide a dark environment for the patient and the DFE equipment 14. In some embodiments, third (left) side 4c will extend at least to the tower table equipment surface 13. In other embodiments, third (left) side 4c may extend down beyond the tower table equipment surface 13 to further block light. In some such embodiments, third (left) side 4c may extend down to the floor or substantially to the floor. Third (left) side 4c may be affixed to the left tower 11 by any suitable fastener, such as hook and loop fasteners, magnets, or an adhesive. Preferably, second (right) side 4b may be temporarily affixed to the dilation tower 1 to permit removal for maintenance, cleaning, etc. of third (left) side 4c. In preferred embodiments where the left patient area cloak arm 9 is extendable/retractable, third (left) side 4c is designed to accommodate the full extension/retraction thereof. Third (left) side 4c may be affixed to left patient area cloak arm 9 by any convenient means to accomplish the goals of blocking light and, where applicable, extension/retraction of the material. For example, the third (left) side 4c may be affixed by hook and loop fastener, adhesive, curtain rings/hooks or similar device, by inserting left patient area cloak arm 9 through third (left) side 4c, etc. Third (left) side 4c may be designed to be stationary (i e, only extendable/retractable when left patient area cloak arm 9 is extended/retracted) or independently extendable/retractable along left patient area cloak arm 9.

Figure 12:
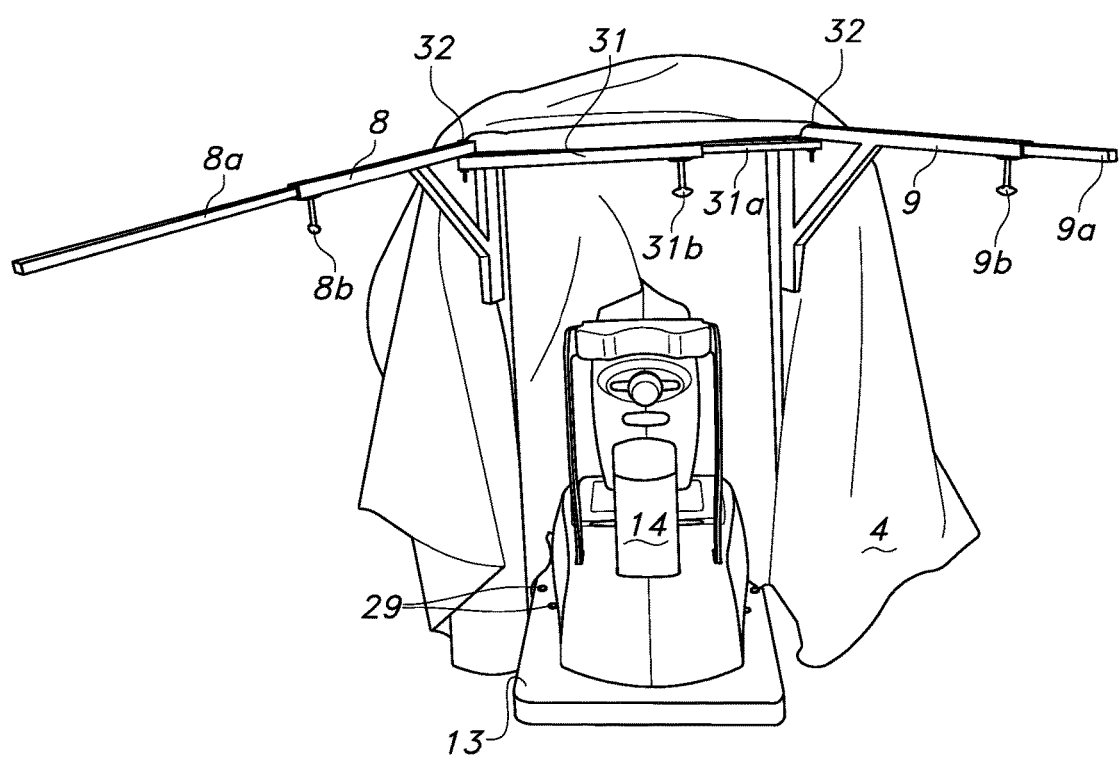
FIG. 12 shows the dilation tower of FIG. 10 from the patient area side with cloak pulled back from adjustable cloak arms in a non-extended (right side) and extended (left side) and swiveled wide position but maintaining cloak first side partitioning medical professional side from the patient area side.

The patient area cloak 4 is designed to have a fourth side 4d, which extends down from between the right and the left patient area cloak arms 8,9. The fourth side 4d should extend down sufficiently to provide a dark environment for the patient and the DFE equipment 14. In some embodiments, fourth side 4d will extend at least to the level of the tower table equipment surface 13. In other embodiments, fourth side 4d may extend down beyond the level of the tower table equipment surface 13 to further block light. In some such embodiments, fourth side 4d may extend down to the floor or substantially to the floor. In some embodiments, fourth side 4d may be an extension of either second (right) side 4b or third (left) side 4c. In these embodiments, fourth side 4d is capable of attaching to the opposite side (4b or 4c) and/or arm (8 or 9), and, preferably, the free edge of fourth side 4d may also be capable of being temporarily affixed the opposite side (4b or 4c) by any suitable fastener, such as hook and loop, magnets, etc. Where fourth side 4d is not an extension of either second (right) side 4b or third (left) side 4c, it is designed to be temporarily attached to either one or both of sides 4b and 4c and arms 8 and 9. In embodiments where the right and the left patient area cloak arms 8,9 are mounted on arm swivel members (such as shown in FIGS. 6-9 and 11-13) and embodiments where the right and the left patient area cloak arms 8,9 can be positioned in narrow/wide configurations (such as shown in FIGS. 5, 11, and 12), fourth side 4d is designed to accommodate a wide variety of widths. Preferably, fourth side 4d may be temporarily affixed to the dilation tower 1 to permit removal for maintenance, cleaning, etc of fourth side 4d.

Figure 10:
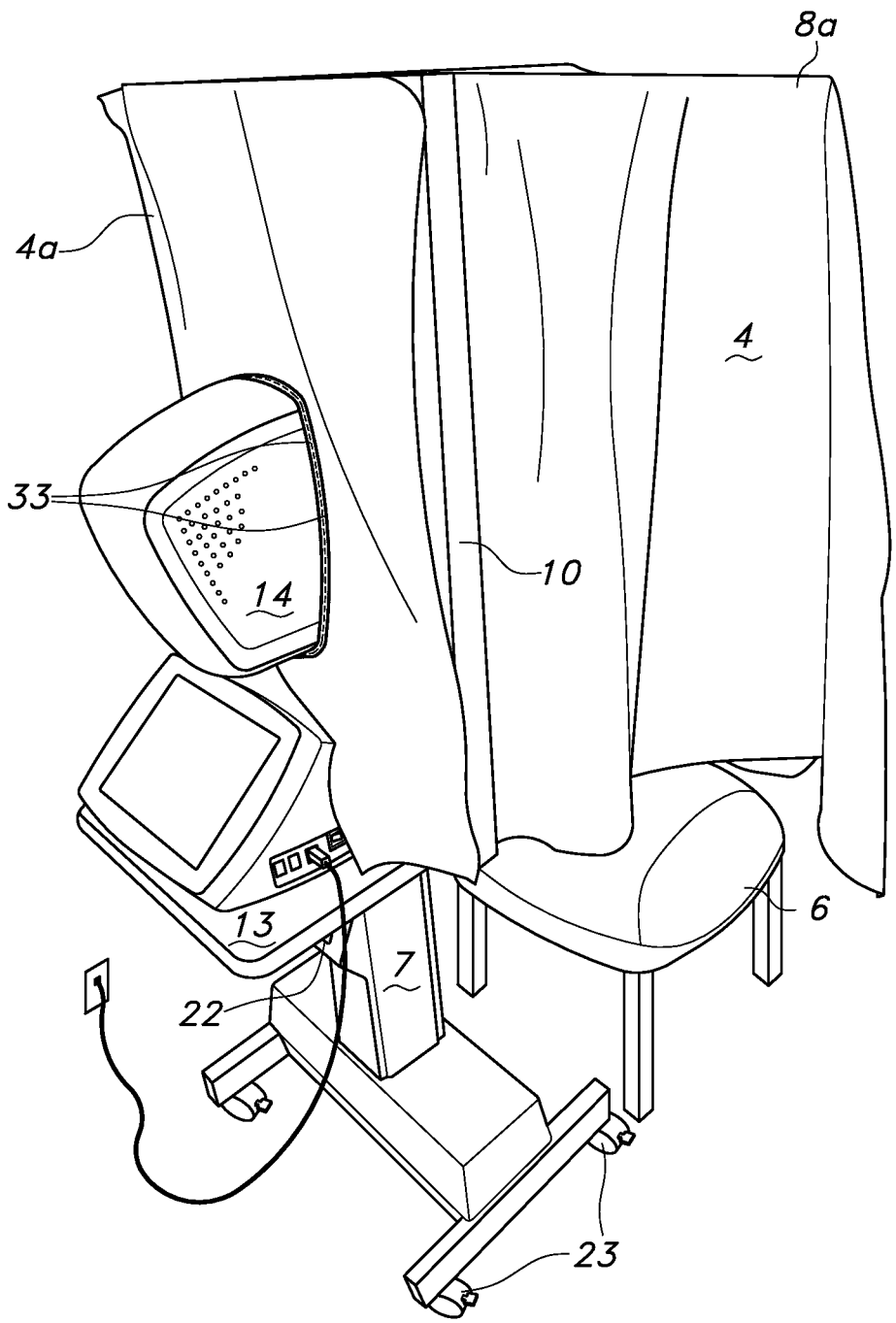
FIG. 10 is another exemplary embodiment of the disclosed dilation tower with patient area cloak having a portal bound in elastic in cloak first side for positioning DFE equipment and maintaining darkness on patient side.

The patient area cloak 4 is designed to have a fifth (top) side 4e, which extends across the top between the right and the left patient area cloak arms 8,9 and from the tower bridge 12 to the ends of the right and the left patient area cloak arms 8,9. In some embodiments, fifth (top) side 4e may be an extension of the first side 4a, the second (right) side 4b, the third (left) side 4c, the fourth side 4d, or any combination of these. Fifth (top) side 4e may be affixed to the right and the left patient area cloak arms 8,9 and/or the tower bridge 12. Preferably, fifth (top) side 4e may be temporarily affixed to the dilation tower 1 to permit removal for maintenance, cleaning, etc. To better prevent light from entering patient area 5 during an examination, the patient area cloak 4 may optionally include flaps or extensions that extend over or across a joint created by a patient area cloak side piece (4a-4e) and/or a physical structure of the dilation tower 1 (e.g., tower bridge 12; right and left tower 10,11; or right and left patient area cloak arms 8,9). In other words, the flap or extension is intended to cover any gaps at an edge of the patient area cloak 4. The flaps can be made from the same material as the patient area cloak side pieces (4a-4e) or from another material entirely. Alternatively, they can be an extension from one or more of these. The flaps can be affixed to the patient area cloak 4 by any suitable means, including sewing, hook and loop, magnets, buttons, zippers, pins, snaps, clasps, hooks, etc. Also, where necessary, a user can position at least the patient side 2 of the dilation tower 1 over a dark, low gloss flooring cover (e.g., a mat) to minimize light reflected from the floor under the patient area cloak 4. As can be appreciated from FIGS. 10-13, the patient area cloak 4 may comprise more than one panel, which advantageously allows for limiting light from the medical professional side 3 entering the patient side 2 during an examination. As shown in FIG. 10, cloak first side/panel 4a is configured to have a portal or opening through which the DFE equipment 14 can extend through on the dilation table 1 from the medical professional side 3 to the patient side 2. Preferably the portal or opening is configured to be held tight against the DFE equipment 14 for limiting light from the medical professional side 3 entering the patient side 2 during an examination, such as lining the portal with an elastic band 33.

Finally, patient area cloak 4 is designed to have at least one opening or entry 15 through which a patient can enter patient area 5. Patient area entry 15 may be positioned anywhere on patient area cloak 4 that is suitable for patient entry into patient area 5. By way of example only, patient area cloak 4 may be configured to have a patient area entry 15 at the meeting of third (left) side 4c and fourth side 4d. Such a configuration could be accomplished by making third (left) side 4c slidable on left patient area cloak arm 9, again by way of example only. Allowing for the patient area entry 15 to be expandable is preferred to better accommodate patients of various sizes without the patient having to come in contact with the patient area cloak all while maintaining a compact footprint of dilation tower 1. Alternatively, patient area cloak 4 may be configured to lift over the right and left patient area cloak arms 8,9 to create the entry 15 for the patient. Some embodiments of dilation tower 1 may further comfortably accommodate patients of various sizes by employing a pivot mechanism 16 attached to the tower bridge 12, as shown in FIG. 5, that allows for expansion of the patient area 5 by pivoting either right or left patient area cloak arms 8,9 or both. Similarly, as shown in FIGS. 6-8 and 11-13, a swivel mechanism 17 located on right and left towers can be used to accomplish the same expansion of the patient area 5 while maintaining a compact footprint of dilation tower 1. Patient area cloak 4 in such embodiments must be designed to accommodate such expansion by containing sufficient material to expand and/or pivot/swivel.

Figure 13:
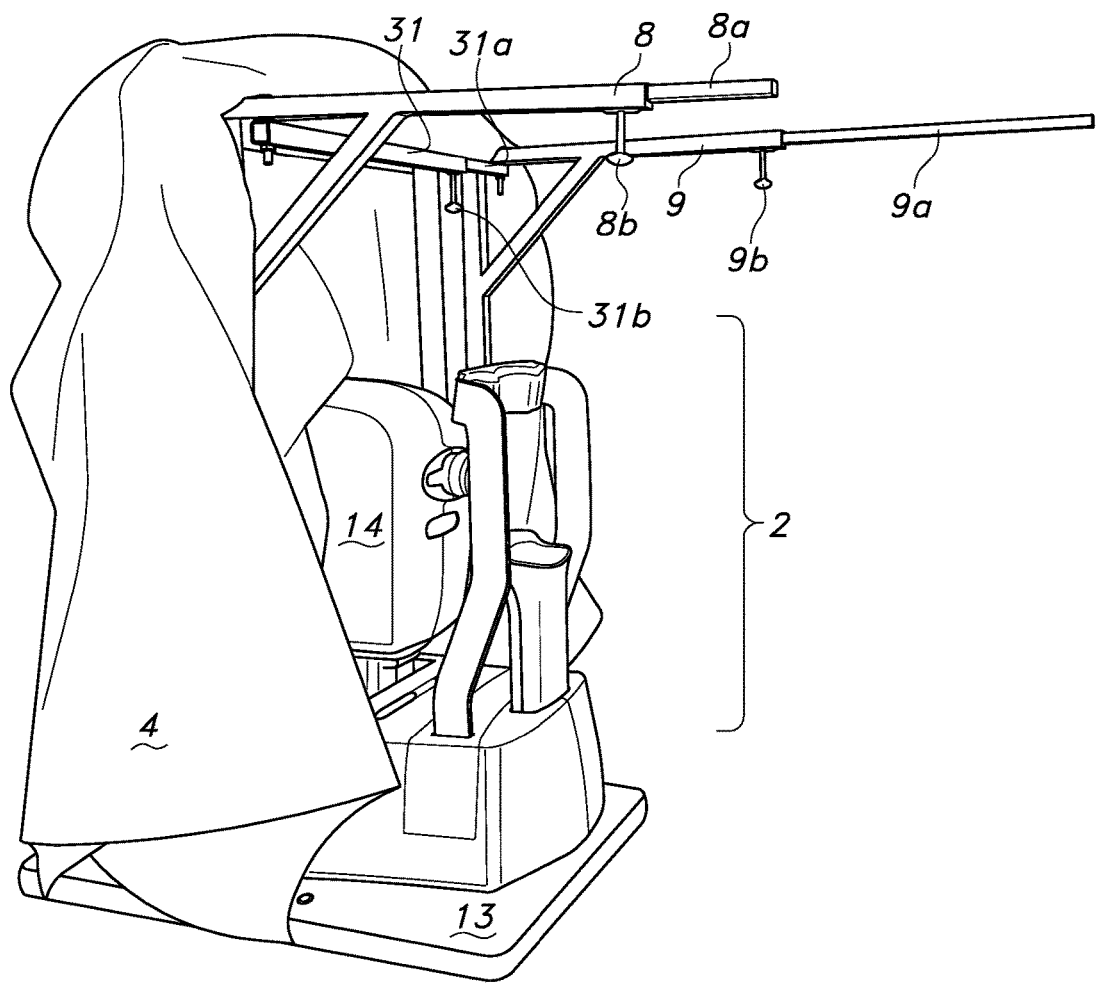
FIG. 13 shows the dilation tower of FIG. 10 from the patient area side with cloak pulled back from adjustable cloak arms in a non-extended (left side) and extended (right side) and swiveled normal position but maintaining cloak first side partitioning medical professional side from the patient area side.

Preferably, right or left patient area cloak arms 8,9 that incorporate a pivot 16 or swivel mechanism 17 include a means to maintain a desired pivot/swivel, such as a set screw 8b/9b, spring, tension rod, and/or other known means. For example, FIGS. 11-13 shows right or left patient area cloak arms 8,9 that incorporate a swivel mechanism 17. In FIG. 11, the right and left patient area cloak arms 8,9 are swiveled to a narrow position (relative to a "normal" position, see FIG. 13). Both extendable arms 8a,9a are held in a non-extended position by set screws 8b,9b by applying pressure to extendable arms 8a,9a. Similarly, the narrow swiveled position is held in place by set screw 31b placed in a cross bar 31 and applying pressure to extendable cross bar 31a. Cross bar 31 and extendable cross bar 31a are affixed to right and left patient area cloak arms 8,9 by fasteners 32. In FIG. 12, the right and left patient area cloak arms 8,9 are swiveled to a wide position (relative to a "normal" position, see FIG. 13). Extendable arm 8a is held in an extended position by set screw 8b, and extendable arm 9a is held in a non-extended position by set screw 9b. The wide swiveled position is held in place by set screw 31b placed in a cross bar 31 and applying pressure to extendable cross bar 31a.

Figure 2:
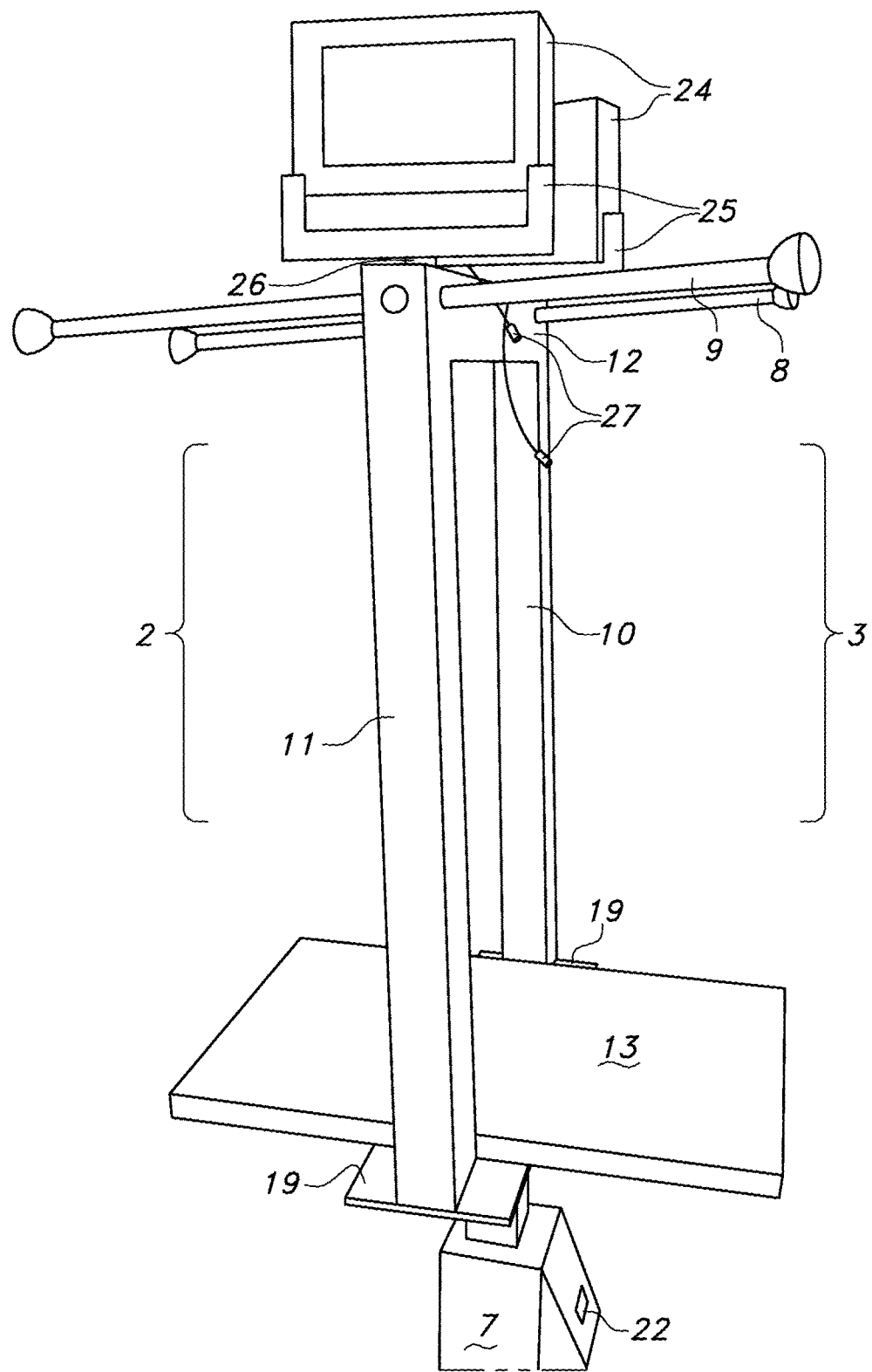
FIG. 2 shows the upper portion of an exemplary embodiment of the disclosed dilation tower.
Figure 4:
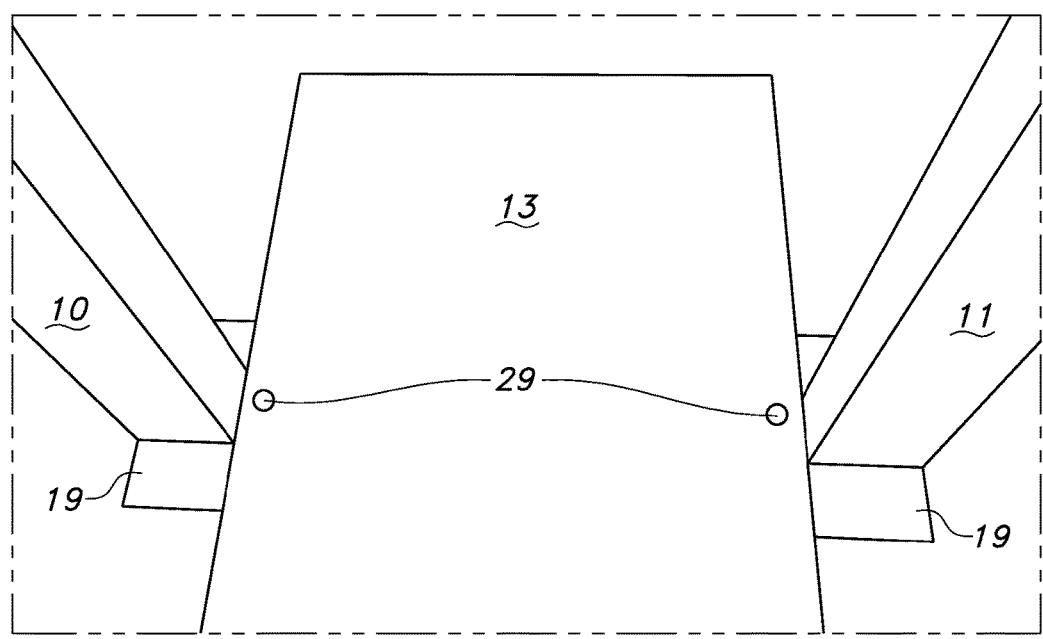
FIG. 4 is a view of the tower table equipment surface.
Figure 6:
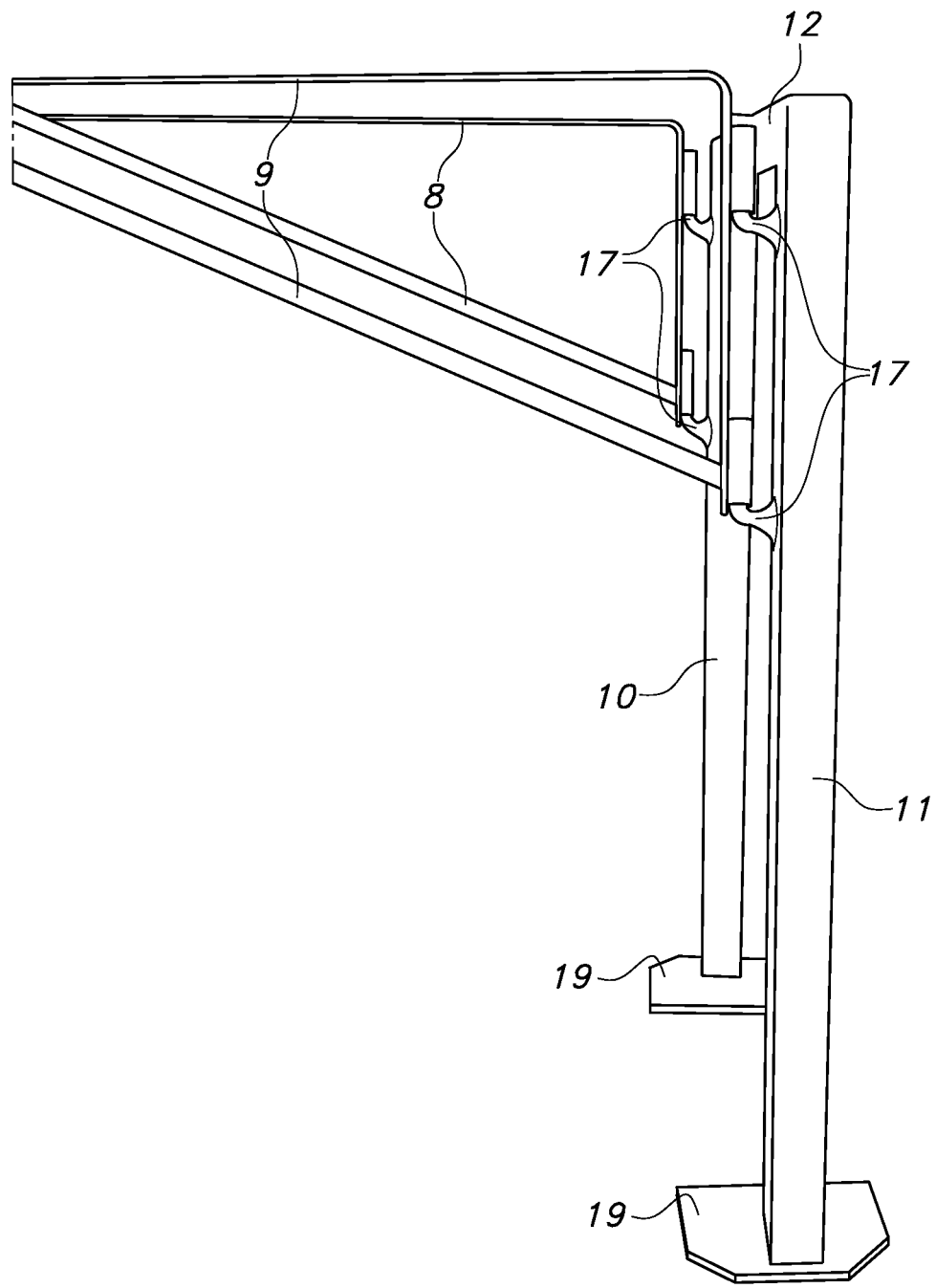
FIG. 6 is another exemplary embodiment of the towers and patient area cloak arms with swivel mounting members.
Figure 8:
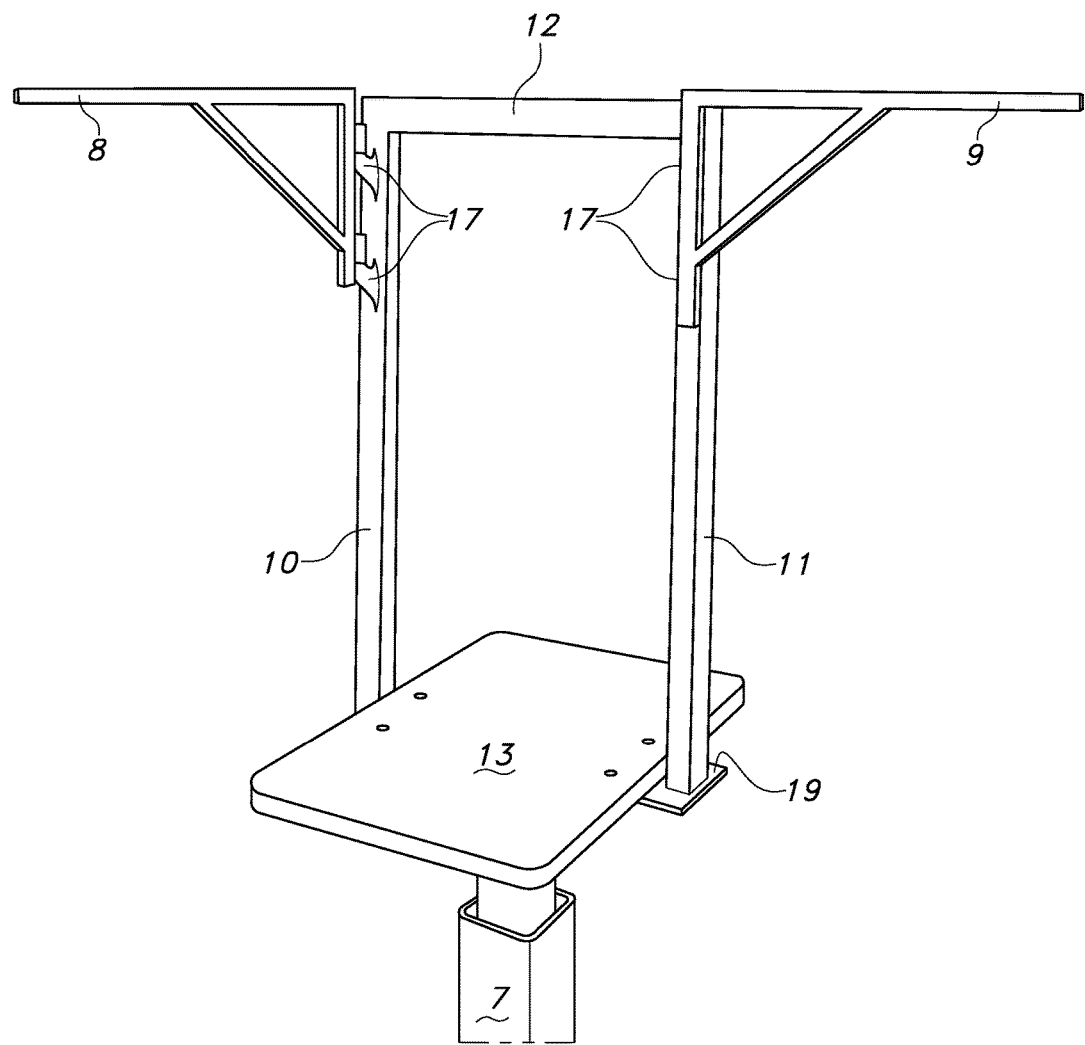
FIG. 8 is the embodiment of the disclosed dilation tower shown in FIG. 7 showing 180° axial positioning of independently extendable patient area cloak arms with swivel mounting members.

Dilation tower 1 is configured to comprise a tower table 18 with equipment surface 13 for holding DFE equipment 14 spanning between patient side 2 and medical professional side 3. Tower table 18 is attached to a tower table base unit 7. Preferably, tower table 18 is height adjustable, as shown in FIGS. 2 and 8, by raising/lowering tower table base unit extension arm 7a. Tower table base unit extension arm 7a may be raised and lowered manually. In some embodiments, tower table base unit extension arm 7a may be raised and lowered pneumatically. In yet other embodiments, tower table base unit extension arm 7a may be raised and lowered mechanically. Tower table 18 also serves to receive right and left towers 10,11 by attachment via tower base plates 19. Tower base plates 19 can be configured to be permanently attached to a tower 10,11, as shown in FIGS. 4 and 6, for example by welding. Alternatively, tower base plates 19 can be configured to receive tower structural members 10a,11a, as shown in FIG. 5. In both configurations, towers 10,11 are affixed to tower table by tower base plate fasteners 29, as shown in FIGS. 4-5. Tower base plate fasteners 29 can be any suitable fastener, for example bolt and nut.

Tower table base unit 7 is optionally equipped with electrical power, as shown in FIGS. 1 and 2. A power cable 20 is supplied for tower table base unit 7 to receive electricity. One or more power outlets 21 are provided in electrically equipped tower table base units 7 for supplying power to the DFE equipment 14, optional multimedia players 24 (discussed below), and/or other equipment. The electrical supply can be centrally controlled by power switch 22. The power switch 22 is preferably located on the medical professional side 3 of dilation tower 1.

In preferred embodiments, tower table base unit 7 contains wheels 23 or other suitable means for mobility. Wheels 23 optionally may contain wheel locks to secure the location of dilation tower 1 when occasionally bumped or otherwise comes into contact with a person (e.g., patient and/or medical professional) or other object. As previously mentioned, one object of the present invention is to reach more patients. The dilation tower 1 of the present invention is designed to accomplish this goal without formal appointments or the intimidation of a formal setting (i.e., doctor's office). We believe the best opportunity to reach out to more patients, especially underserved populations, is to provide a compact, mobile dilation tower of the present invention in high traffic pedestrian environments, such as malls, large stores, and/or shopping centers. Use of wheels 23 or mobility means allows better access and mobility to and within such target environments.

Figure 3:
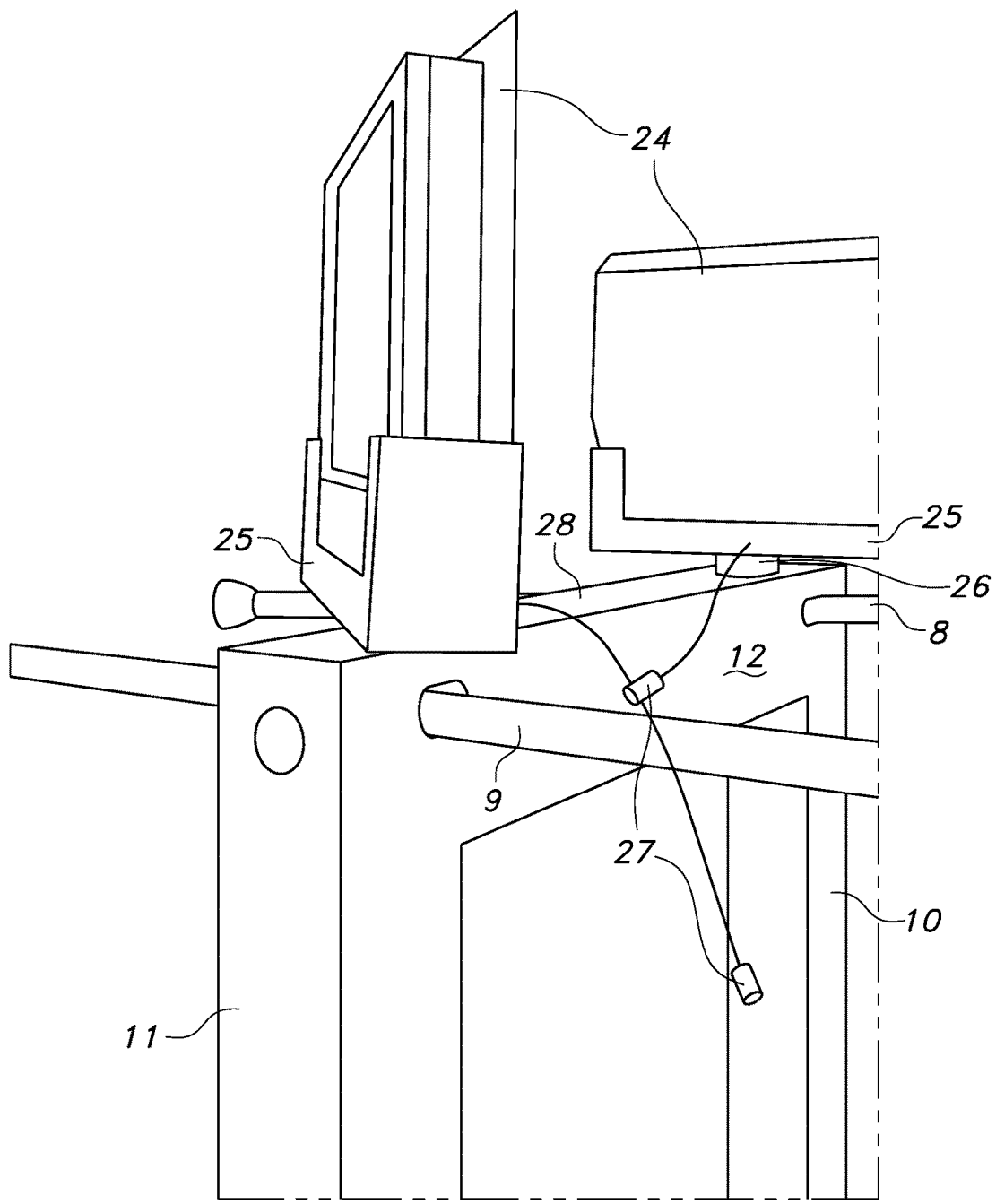
FIG. 3 is a view of the bridge and multimedia player holders of an exemplary embodiment of the disclosed dilation tower.

Now referring to FIG. 3, the tower bridge 12 is preferably configured to contain a platform 28 for attaching multimedia players 24. Multimedia players 24 may be provided for in situ audio-visual marketing of the dilation tower 1 and services associated with it. Multimedia players 24 could also be used for marketing other services and locations of the medical professional user of the dilation tower 1. Alternatively, multimedia players 24 can be used to market products and/or services unrelated to the medical professional user or the dilation tower 1. Multimedia players 24 are held fast to dilation tower 1 by multimedia holders 25. Holders 25 are preferably configured to securely receive multimedia players 24, while also allowing multimedia players 24 to be removed by authorized personnel (e.g., by key or electrical security means). As a primary marketing tool, multimedia holders 25 are preferably mounted onto bridge platform 28 by a multimedia base 26. Multimedia base 26 may contain a swivel to allow multimedia players 24 to be rotated around the axis of the swivel base 26 to be positioned in an optimal direction to attract potential patients around the dilation tower 1. Multimedia player electrical wires 27 may be necessary for some models to provide continuous electrical power to multimedia players 24. So that the wires 27 do not simply hang down and possibly interfere with the examination, tower bridge 12 and right and left towers 10,11 are preferably configured to be hollow and act as a conduit for wires 27 from multimedia players to power outlets 21 on tower table base unit 7 or other sources of electricity. One or more access holes 30 for the tower bridge 12 electrical conduit is/are provided on bridge platform 28. In embodiments comprised of right and left tower structural members 10a,11a, right and left tower covers 10b,11b provide concealment of the wires 27 as a conduit.

Figure 9:
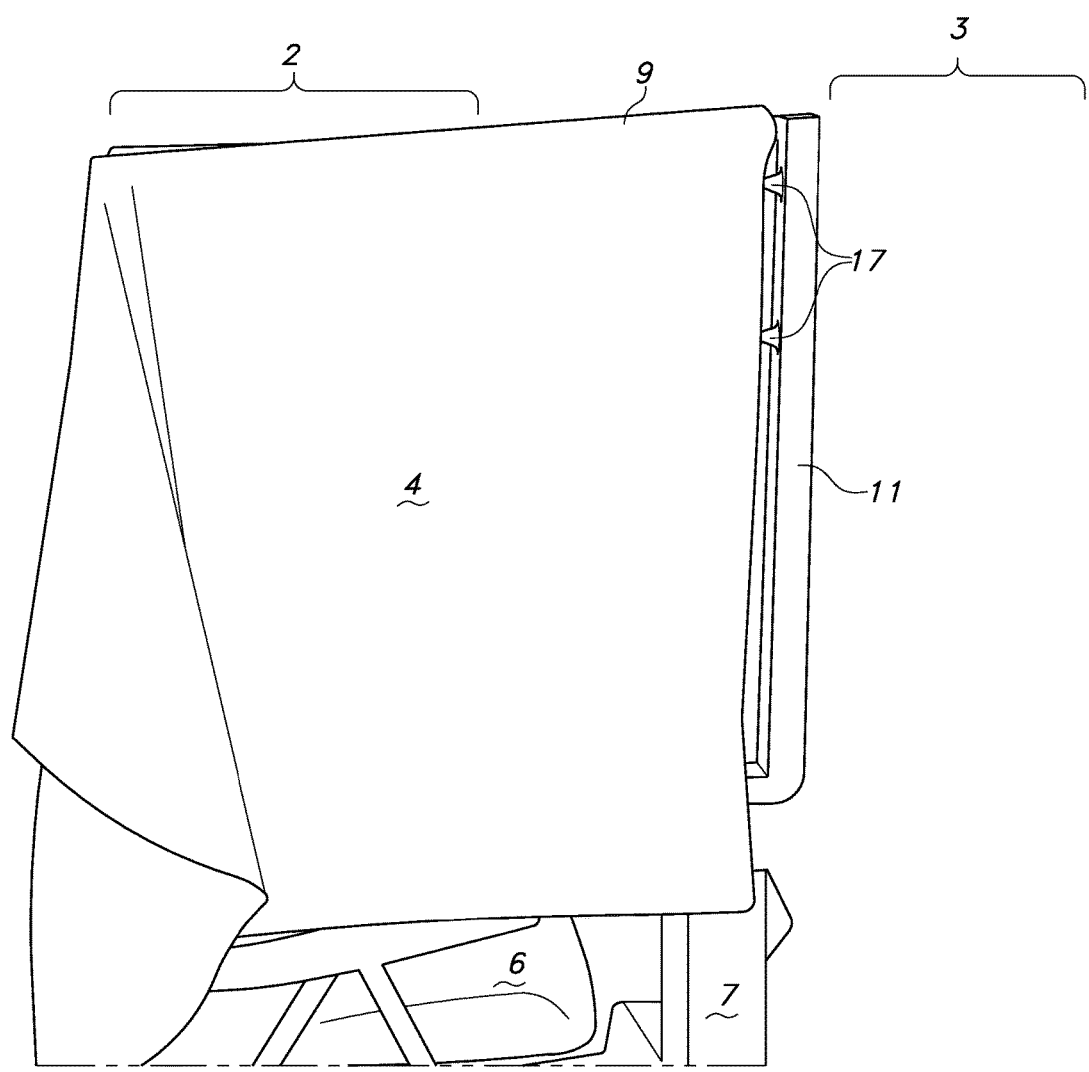
FIG. 9 is the embodiment of the disclosed dilation tower shown in FIG. 7 with patient area cloak extended over patient area.

Referring to FIG. 4, tower table 18 is designed to provide an equipment surface 13 with sufficient dimensions for DFE equipment (not shown) to span across patient side 2 and medical professional side 3, while also providing attachment and support for right and left towers 10,11 via tower base plates 19 and fasteners 29. Preferably, base plates 19 and fasteners 29 take up little, if any, of tower table equipment surface 13. Referring now to FIG. 5, DFE equipment 14 is shown placed on dilation tower 1 spanning across patient side 2 and medical professional side 3. The medical professional may adjust the right and left patient area cloak arms 8,9 according to the needs of the patient. As shown in FIG. 5, the right and left patient area cloak arms 8,9 can be adjusted laterally toward/away from the right and left towers 10,11, by extension of right and left patient area cloak arms 8,9, and/or axially about pivot 16 for larger patient area 5 needs. For embodiments having right and left patient area cloak arms 8,9 sitting on swivel members 17, such as in FIGS. 6 and 7, the medical professional may adjust the arm extensions 8a,9a (FIG. 7) or the arms 8,9 about the swivel members 17 (FIG. 8), as necessary (FIG. 9). As shown in FIG. 8, right and left patient area cloak arms 8,9 may expand to 180 degrees or more (relative to one another and the towers); however, this position is not practical with patient area cloak 4 attached to define the patient area 5.

Another object of the present invention is to provide a method for administering a DFE to a patient in a bright environment utilizing a dilation tower 1 as described above. The medical professional will position the patient in the patient area 5. To wit, the patient may enter patient area 5 by an entry in patient area cloak 4 and be seated in patient seat 6. Once the patient has been seated, the medical professional will then enclose (i.e., secure) the patient area cloak 4 to provide a dark environment for the DFE. This step may optionally include ensuring that all seams are closed by overlapping the cloak 4 or by securing any optional flaps. By securing patient area cloak 4, the medical professional can perform the DFE without the need of mydriatic agents (e.g., tropicamide) even in otherwise bright environments. Non-mydriatic examinations are preferred for the present invention because the patient will not suffer from dilated pupils and light sensitivity following the examination. As necessary, the height of tower table 18 may be adjusted up or down. The medical professional can sit or stand at or near the medical professional side to conduct the examination (administer the DFE to the patient). In preferred embodiments, DFE equipment 14 is utilized that allows automatic and rapid DFEs for one or both eyes of the patient. After exiting the patient area 5, patient and medical professional may review the results of the examination at the medical professional side 3 of DFE equipment 14, on a computer device (computer, laptop, tablet, smart phone, etc.), and/or the results can sent electronically (e.g., email) directly to the patient or the patient's primary care physician for records and/or follow-up.

The terms "comprising," "including," and "having," as used in the claims and specification herein, shall be considered as indicating an open group that may include other elements not specified. The terms "a," "an," and the singular forms of words shall be taken to include the plural form of the same words, such that the terms mean that one or more of something is provided. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example and not of limitation.

While the invention has been described with respect to a limited number of embodiments, those skilled in the art, having benefit of this disclosure, will appreciate that other embodiments can be devised which do not depart from the scope of the invention as disclosed herein. For example, the dilation tower of the present invention could be configured to have an enclosed, but expandable cell defining the patient area. Accordingly, the scope of the invention should be limited only by the attached claims.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

We claim:

1. A dilation tower comprising a right tower, a left tower, a tower table base unit, a tower table, a patient side, wherein the patient side comprises a patient area defined by a patient area cloak, and a medical professional side.

2. The dilation tower of claim 1, wherein said tower table base unit is configured for mobile transport of said dilation tower.

3. The dilation tower of claim 1, further comprising automatic DFE equipment.

4. The dilation tower of claim 1, wherein said tower table is height adjustable.

5. The dilation tower of claim 1, wherein said patient area cloak is configured to extend to the surface of said tower table.

6. The dilation tower of claim 1, wherein said patient area cloak is configured to extend to a floor surface.

7. The dilation tower of claim 1, wherein said patient area cloak is supported at least in part by patient area cloak arms.

8. The dilation tower of claim 7, wherein said patient area cloak arms are extendable and retractable.

9. The dilation tower of claim 7, wherein said patient area cloak arms are independently extendable and retractable.

10. The dilation tower of claim 7, wherein said patient area cloak arms are configured to move about a tower bridge to expand or contract said patient area.

11. The dilation tower of claim 7, wherein said patient area cloak arms are configured to swivel to expand or retract the patient area.

12. The dilation tower of claim 7, wherein said patient area cloak arms are configured to pivot to expand or retract the patient area.

13. The dilation tower of claim 1, further comprising at least one multimedia player.

14. The dilation tower of claim 1, further comprising a patient seat in the patient area.

15. The dilation tower of claim 1, further comprising a power cable to receive electrical power.

16. A method of administering a DFE to a patient in a bright environment comprising the steps of positioning said patient in a patient area of a dilation tower according to claim 1, enclosing said patient and said patient area with a patient area cloak, and performing said DFE on said patient.

17. The method of claim 16, further comprising the step of adjusting a tower table up or down.

18. The method of claim 16, further comprising the step of reviewing the DFE results with said patient.

19. The method of claim 16, further comprising the step of electronically sending the DFE results.

* * * * *